United States Patent

Park

[11] Patent Number: 6,157,199
[45] Date of Patent: Dec. 5, 2000

[54] METHOD OF MONITORING ION-IMPLANTATION PROCESS USING PHOTOTHERMAL RESPONSE FROM ION-IMPLANTED SAMPLE, AND MONITORING APPARATUS OF ION-IMPLANTATION PROCESS

[75] Inventor: Sun-jin Park, Kyungki-do, Rep. of Korea

[73] Assignee: Samsung Electronics Co., Ltd., Suwon, Rep. of Korea

[21] Appl. No.: 09/184,853

[22] Filed: Nov. 3, 1998

[30] Foreign Application Priority Data

Dec. 26, 1997 [KR] Rep. of Korea ...................... 97-74377

[51] Int. Cl.⁷ ........................... H01L 21/66; G01N 21/00; G01R 31/308
[52] U.S. Cl. ................... 324/752; 324/501; 250/492.21; 250/492.2; 437/20; 437/7
[58] Field of Search ............... 250/492.21, 492.2; 437/20, 7; 324/501, 752

[56] References Cited

U.S. PATENT DOCUMENTS

| | | | |
|---|---|---|---|
| 5,185,273 | 2/1993 | Jasper | 437/8 |
| 5,228,776 | 7/1993 | Smith et al. | 374/5 |
| 5,408,327 | 4/1995 | Geiler et al. | 356/432 |
| 6,081,127 | 6/2000 | Wagner et al. | 324/765 |

*Primary Examiner*—Bruce C. Anderson
*Assistant Examiner*—Nikita Wells
*Attorney, Agent, or Firm*—Jones Volentine

[57] ABSTRACT

A method and apparatus of monitoring an ion-implantation process include a precise analysis for the process conditions of the ion-implantation process by processing the detected signals by using frequency response characteristics of plasma and thermal waves generated by irradiating an ion-implanted surface with a laser beam. The monitoring includes: counting a complex conversion coefficient from the each result value measured for the photo-thermal response by irradiating a laser beam on the sample into which ions are implanted by changing a specific process condition of the ion-implantation process; linearizing a specific parameter of complex conversion coefficient for each value of the complex conversion coefficient according to the changes of the specific process condition; and monitoring a value of the specific process condition of the ion-implantation process based on a detected value of the specific parameter which is linearized according to the changes of the specific process condition.

17 Claims, 4 Drawing Sheets

METHOD OF MONITORING ION-IMPLANTATION PROCESS USING PHOTOTHERMAL RESPONSE FROM ION-IMPLANTED SAMPLE, AND MONITORING APPARATUS OF ION-IMPLANTATION PROCESS

CROSS-REFERENCES TO RELATED APPLICATIONS

The present application claims priority under 35 U.S.C. §119 to Korean Patent Application No. 97-74377 filed on Dec. 26, 1997, the entire contents of which are hereby incorporated by reference.

BACKGROUND OF THE INVENTION

1. Field of the Invention

The present invention relates to a method of monitoring ion-implantation process, and a monitoring apparatus using the same. More particularly, the present invention is directed to a method of monitoring an ion-implantation process using photo-thermal response from an ion-implanted sample in order to improve the analysis for process conditions of ion-implantation process, such as ion-dose or ion-implantation energy, by using the frequency response characteristics of the plasma and thermal waves generated by the excitation of the ion-implanted portion, and a monitoring apparatus using the same.

2. Description of Related Art

Generally, in the semiconductor device fabrication process, ion-implantation is carried out in order to implant impurities on a certain active area or insulating area, and change the electrical characteristics of the corresponding areas.

The ion-implantation requires precise setting of process conditions and controls therefor in order to achieve desired electrical characteristics on a semiconductor wafer. In general, the dose on the ion-implanted sample and the uniformity of the ion-implantation are the main factors for setting the process conditions and the controls therefor exactly.

Conventionally, the ion-dose and the uniformity are detected by measuring sheet resistivity. This method requires the performance of an annealing process after implanting ions on the wafer. However, the annealing process takes lots of time, and the above measurement method cannot be applied on the wafer having a specific pattern formed thereon.

In order to address these problems, the inspection method for the ion-dose and the uniformity using a photo-thermal response technology was newly introduced, and the U.S. Pat. No. 4,632,562 and the U.S. Pat. No. 5,408,327 disclose the analysis of a sample using photo-thermal response technology, both of which are hereby incorporated by reference in their entirety.

In the photo-thermal response technology, if a modulated laser beam is absorbed on the ion-implanted sample, plasma and thermal waves are generated by excitation of the sample. At this time, frequency differences between the two waves occur, which is used in the analysis for the ion-implantation process.

In other words, during the ion-implantation, damage often occurs on the surface of the sample according to the dose of the impurities and the energy. If a modulated laser beam is irradiated on the surface of the sample for the analysis of the ion-implantation process, a modulated laser beam is absorbed on the damaged portion, and plasma and thermal waves are generated by excitation. The generated plasma and thermal waves change the reflectivity of the surface of the wafer, and the detected results, i.e., the response characteristics, have phase shifts representing a time delay between the amplitude of the changed reflectivity and the excitation.

The response characteristics are measurement parameters for analyzing the dose for the sample and the uniformity, with "K" as the plasma wave parameter, and "R" as the reflectivity parameter are derived from the response characteristics, which are used for the analysis. The thermal wave parameter is K (complex conversion coefficient), which is used for the analysis of ion-dose.

In the analysis using the K (complex conversion coefficient), the amplitude and the phase shift of the K (complex conversion coefficient) according to the variance of the ion dose show a certain range which can be seen as curve-shape as a second-order function graph. However, it is difficult to judge the process conditions for controlling the ion dose precisely just by means of the above graph for K (Complex Conversion Coefficient) with the curve-shape as described above. Fine variations in the signal corresponding to the imaginary part of the curve may cause a great difference in the variance of the ion dose corresponding to the real part thereby making it difficult to precisely analyze.

Therefore, the measurement of the dose of the implanted ions using the above method cannot be accurately applied in the analysis for the ion-implantation and the facility.

SUMMARY OF THE INVENTION

The present invention is therefore directed to a method of and an apparatus for monitoring the ion-implantation process which substantially overcomes one or more of the problems due to the limitations and disadvantages of the related art.

The present invention is directed to providing a method of monitoring ion-implantation process by linearizing a specific parameter of a thermal wave parameter (the complex conversion coefficient, K) derived for the response characteristics by the frequency difference between the plasma and thermal waves generated by excitation from a modulated laser beam-absorbed sample, and converting the specific parameter to a first-order function relation which is in one-to-one correspondence with the process conditions of the ion-implantation process, such as a dose, etc.

Another object of the present invention is directed to provide a monitoring apparatus of ion-implantation process based on the linearization of a specific parameter of a thermal wave parameter (the complex conversion coefficient, K) derived as the response characteristics by the frequency difference between the plasma and thermal wave generated by excitation according to the absorption of a modulated laser beam to a sample.

To achieve these and other advantages and in accordance with purpose of the present invention, the method of monitoring ion-implantation process using photo-thermal response from an ion-implanted sample includes: counting a complex conversion coefficient from each of the result values measured for the photo-thermal response by irradiating a laser beam on the sample into which ions are implanted changing specific process conditions of the ion-implantation process; linearizing a specific parameter of complex conversion coefficient for each value of the complex conversion coefficient according to the changes of the process conditions; and monitoring the changes of the specific process conditions of the ion-implantation process based on the specific parameter which is linearized according to the changes of the process conditions.

The specific process condition of the ion-implantation process, which is changed, may be a dose of ions or an energy of ions. The specific parameter of the complex conversion coefficient, which is linearized, maybe a distance between each indicating point of each of the complex conversion coefficient in a complex coordinates.

The linearizing a specific parameter of each of the complex conversion coefficient according to the changes of the process conditions includes: designating each of the complex conversion coefficients in complex coordinates; detecting the traces between each of the indicating points of the complex conversion coefficients on the complex coordinates; counting the moving distance of the traces between each of indicating points responsive to the changes of the process conditions; and designating the moving distance of the traces between each of indicating points responsive to the changes of the process conditions on a graph.

The detecting of the traces between each of the indicating points of the complex conversion coefficients may be carried out by converting the indicating point (real part, imaginary part) of each of the complex conversion coefficients designated in complex coordinates into a rectangular coordinate value (X,Y) in rectangular coordinates.

The counting of the moving distance of the traces may be performed by setting an initial value corresponding to an initial condition of the process condition, which is changed, counting the moving distance of the traces according to the changes of each of the process conditions, and summing the initial value and the increase of the moving distance.

The moving distances of the traces, which are shown as a graph, are designated as a first order function, which is in a one-to-one correspondence with the changes of the process conditions.

In another aspect of the present invention, a monitoring apparatus of an ion-implantation process using photo-thermal response from an ion-implanted sample, wherein the ion-implanted sample is irradiated with a laser beam, the monitoring apparatus includes: a detector for measuring a photo-thermal response from the ion-implanted sample; a complex conversion coefficient counter which counts a complex conversion coefficient from a plurality of result values measured from the detector; and a linearizer which linearizes a specific parameter of the complex conversion coefficient for each of the complex conversion coefficients according to the variance of the process conditions of the ion-implantation process. The apparatus may include a display which displays the changes of a specific process condition of the ion-implantation process based on a specific parameter which is linearized by the linearizer.

The linearizer may include a processor which designates each of the complex conversion coefficients in complex coordinates; detects the traces of each indicating point of the complex conversion coefficient in complex coordinates; and counts the moving distance of the indicating point of the complex conversion coefficient on the traces according to the variance of the process condition. The processor may also make a graphical representation of the moving distance of the indicating points on the traces according to the variance of the process condition.

It is to be understood that the both foregoing general description and the following detailed description are exemplary and explanatory and are intended to provide further explanation of the invention as claimed.

BRIEF DESCRIPTION OF THE DRAWINGS

The foregoing and other objects, aspects and advantages will be described with reference to the drawings, in which.

DETAILED DESCRIPTION OF THE PREFERRED EMBODIMENTS

Reference will now be made in detail to the preferred embodiments of the present invention, examples of which are illustrated in the accompanying drawings.

In the embodiment of the present invention, when the dose of the ion-implanted sample is analyzed using an ion-implantation analysis facility, a necessary analysis standard as the complex conversion coefficient is set, and the ion-implanted wafer is irradiated with a laser beam according to the set analysis standard. As a result, a signal having a certain frequency is detected, and the ion-implantation process can be monitored based on the detected signals.

First, the method of monitoring ion-implantation process according to the present invention will be described in detail referring to the process sequence of FIG. 4B.

Ions are implanted on a sample in an ion-implantation facility (not shown) such that the ion-implanted sample is set to have a certain dose in advance (S2), and a certain signal is detected by irradiating the ion-implanted sample with a laser beam (S4).

In the analysis facility (not shown) for the measurement according to the embodiment of the present invention, a photo-thermal response principle is used, and further, an analysis facility using a photo-thermal heterodyne principle having a complex conversion coefficient can be used. The analysis facility employing the photo-thermal response principle may have a different light source depending on its manufacturer, but in a specific example, an analysis facility having laser diode light source operating a wavelength of 785 nm, which generates one single beam with two excitation frequencies, may be used.

Figure 1:
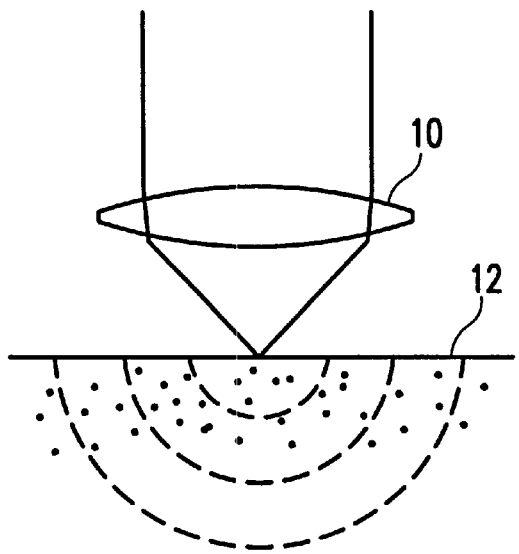
FIG. 1 is a cross-sectional view showing that a modulated laser beam is scanned on an ion-implanted sample.
Figure 2:
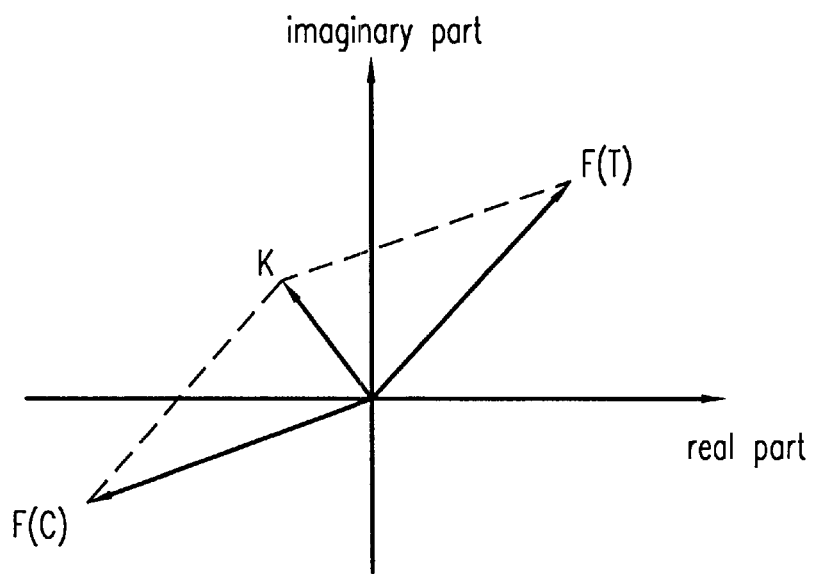
FIG. 2 is a graphical representation of complex conversion coefficient designated in complex coordinates.

In the measurement step (S4), a laser beam from a light source is focused through a collect lens 10 on an ion-implanted portion of the sample surface 12 as shown in FIG. 1, and the power of the laser beam is absorbed on the surface of the sample 12 which is damaged by the ion-implantation.

In other words, the surface of the sample is damaged by the implanted ions, that is, when ions having electrical characteristics are implanted on the sample, the ions collide with the molecules of the sample. As a result, the distortion in the linkages of the sample molecules occurs, and electrons and holes are produced due to the changes of the linkages of the molecules.

Then, the damaged sample surface absorbs power of the laser beam focused on the damaged portion, and as a result, plasma and thermal waves are produced by excitation because of the changes of the energy state of the molecules, or the combination of electrons and holes.

Then, there occurs a known photo-thermal response for the plasma and thermal waves having a frequency identical to the excitation frequency difference of the plasma and thermal waves, and the photo-thermal response is modified-shown as thermal wave parameter, K (complex conversion coefficient). The complex conversion coefficient is shown as functional relation of the thermal and plasma waves(or charge-carrier wave) having complex components. The thermal wave is designated as complex function, F(T) and the charge-carrier wave is designated as complex function, F(C). Therefore, the complex conversion coefficient, K is designated as complex function by the vectorial superposition of the two functions, and the results are shown in the complex coordinates shown in FIG. 3 in which a real part axis and an imaginary part are perpendicular (S6). That is, K=F(T)+F(C).

When the measurement for the ion-implanted sample is completed with a specifically-set dose of ions as described above, the above S2 to S6 are repeatedly carried out while varying the dose of ions, and from each measurement value acquired according to the variance of the dose of ions, a complex conversion coefficient is counted, which can be designated in complex coordinates. Alternatively, if the energy is the parameter of interest, the above calibration maybe performed by varying the energy at set levels.

Figure 5:
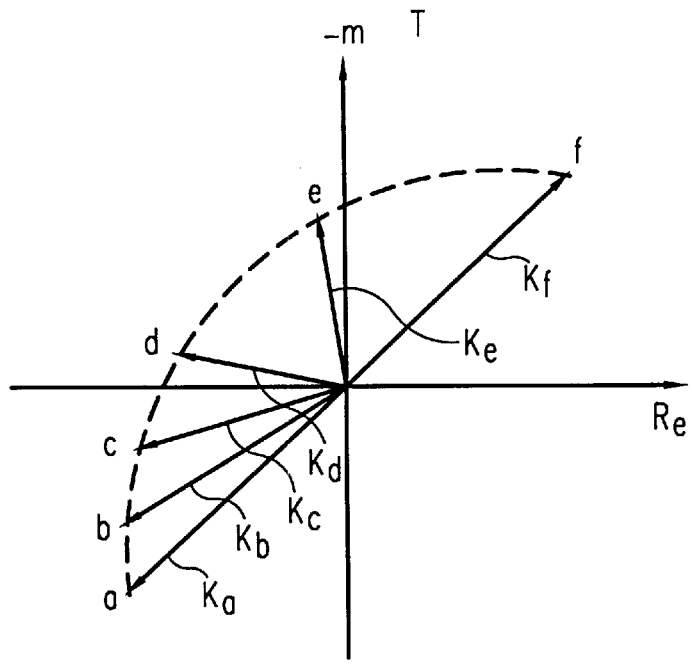
FIG. 5 is a graphical representation showing the trace of complex conversion coefficient in complex coordinates for the analysis ranges of a specific process condition to be monitored according to one embodiment of the present invention.

At this time, increasing the dose of the ions according to the set dose from the initial condition to the final condition, a plurality of complex conversion coefficients, K, are obtained and are designated in complex coordinates. As shown in FIG. 5, with the dose of ions varied from "a" to "f", the complex conversion coefficient values are changed from "Ka" to "Kf", and the magnitudes and phases of each complex conversion coefficient are gradually changed.

Figure 3:
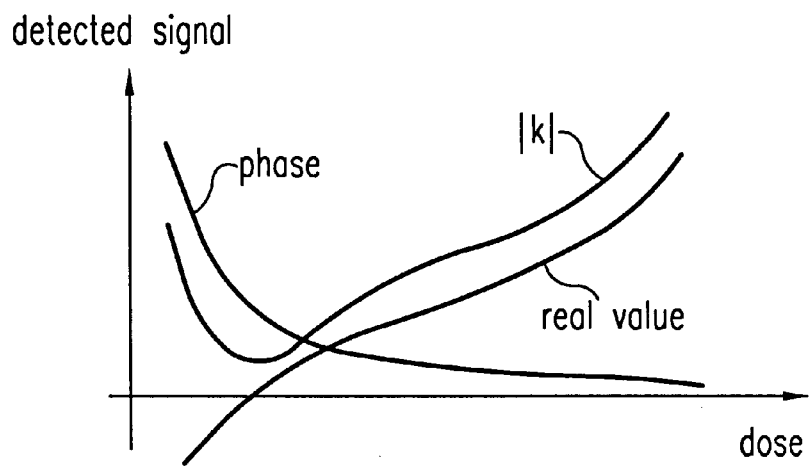
FIG. 3 shows graphical representations of the changes of phase, magnitude, and real value of complex conversion coefficient according to the variance of the dose respectively.

Detecting the photo-thermal response for the ion-implanted sample with the variance of dose of ions as described above, graphs of phase (imaginary values), magnitude (|K|), and real values of the detected signals for the plurality of complex conversion coefficient values according to the variance of the dose of ions ranging from "a" to "f" are shown in FIG. 3 respectively.

As shown in FIG. 3, since the variance of a phase, a magnitude, and a real value of the complex conversion coefficient shows a specific curve ranges of multiple functions respectively, the process conditions of the ion-implantation process, especially the changes of the dose of ions, cannot be analyzed exactly just with the detected signals as above.

Figure 4A:
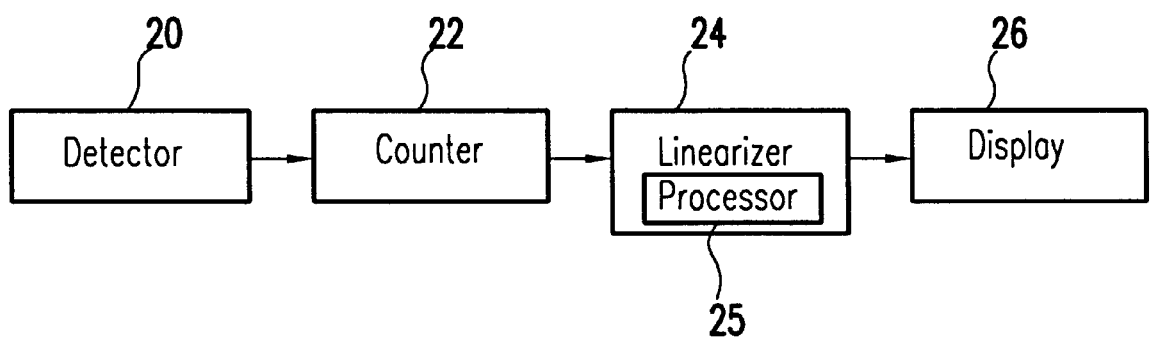
FIG. 4A is a block diagram of one embodiment of the ion-implantation monitoring apparatus of the present invention.
Figure 4B:
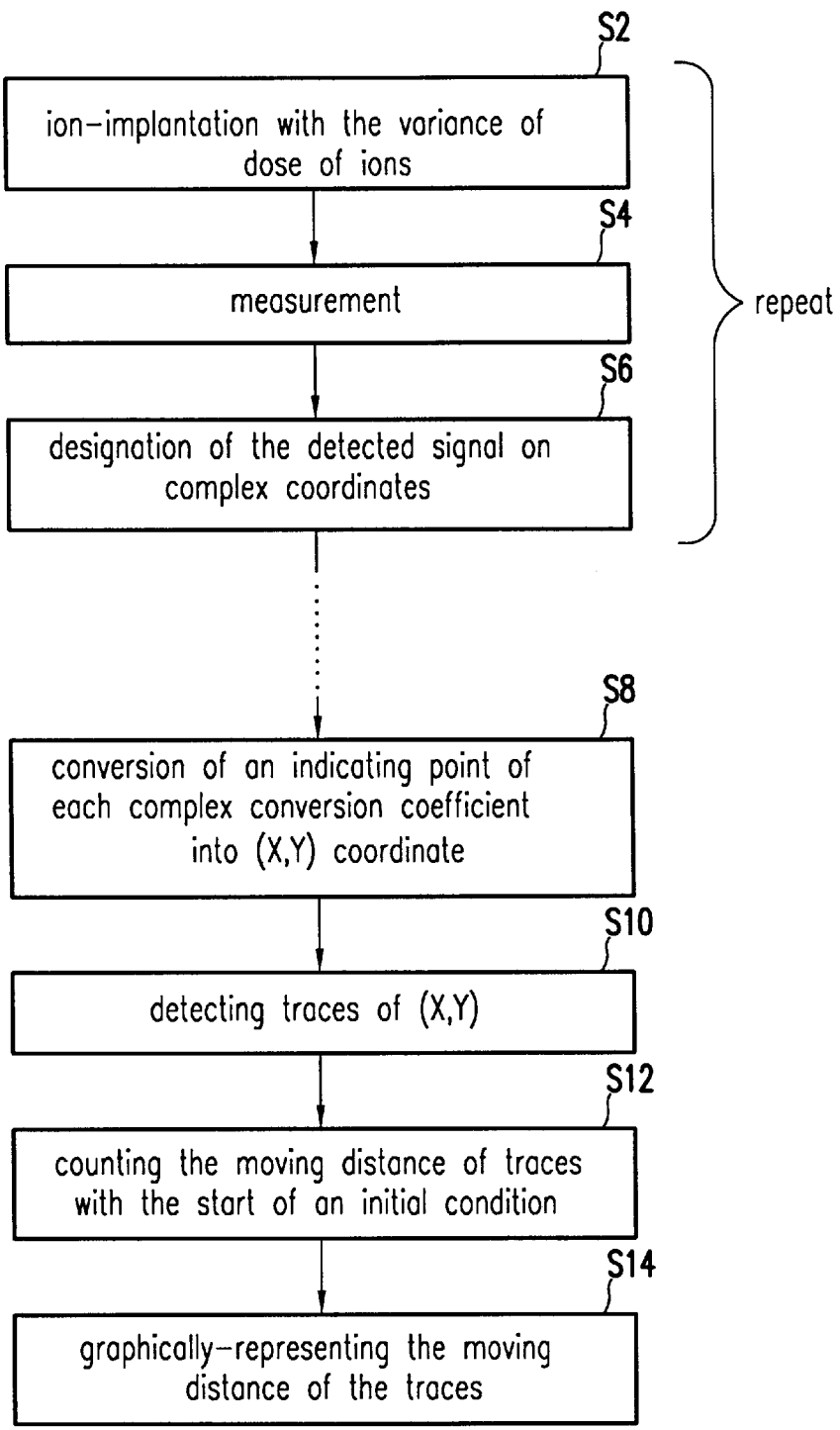
FIG. 4B is a process sequence showing one embodiment of the method of monitoring ion-implantation process for an ion-implanted sample using photo-thermal response according to the present invention.

Then, referring to FIG. 4B, an indicating point (end point) of each of the complex conversion coefficient from "Ka" to "Kf", which can be designated as (real part, imaginary part) in complex coordinates, is converted into (X,Y) coordinate in rectangular coordinates (S8). Then, the traces of rectangular coordinate (X,Y) for each indicating point according to the sequential variance of the dose of the ions (a→b) are detected (S10).

Then, an arbitrary value, e.g., "100", is set as the constant of the dose of the initial condition for the ion-implanted sample, a moving distance of the traces of the coordinate (X,Y) of each complex conversion coefficient is counted (S12). Then, the counted result and the arbitrary value set for the initial condition are added. That is, if the moving distance of the traces, which is counted according to the variance of the dose after the initial condition, is "20", and the arbitrary value is "100", the new value "120" comes out as result by summing the increase of the moving distance of the traces for the corresponding dose "20".

Figure 6:
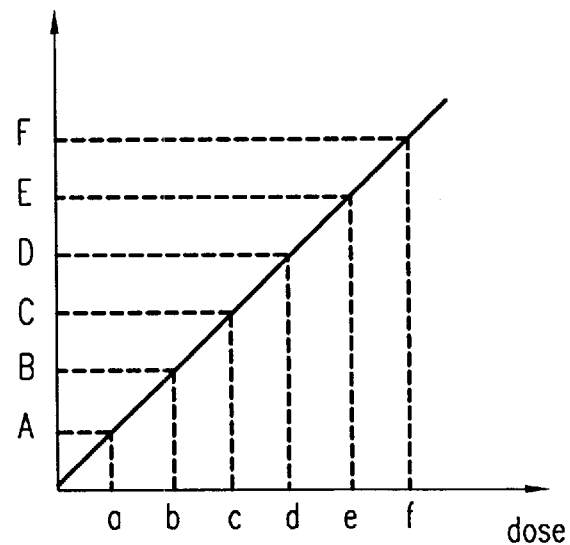
FIG. 6 is a graphical representation showing the correlation of the moving distance of the traces and the variance of the dose of implanted ions according to one embodiment of the present invention.

When corresponding each of the doses set forth above to the magnitude of the moving distance of the traces, that is, a→f and A→F, a graphical representation can be achieved as shown in FIG. 6. Referring to FIG. 6, the moving distance of the traces is proportional to the gradual increase of the dose and the dose, and the moving distance of the traces counted from the detected signals have one-to-one correspondence, first-order functional relationship, which can be the analysis standard for the dose of the ion-implantation.

Accordingly, the monitoring standard for the process analysis of the ion-implantation process can be set-up as described above, in such a manner that the complex conversion coefficient in complex coordinates is converted into the value in rectangular coordinates, the traces according to each dose are detected in the conversion state, the moving distance of the traces for the increase of the dose is counted, and a graphical representation for the counted distance values is made.

As shown in FIG. 4A, in another aspect of the present invention, the monitoring apparatus of the ion-implantation process employs the above method of monitoring the ion-implantation process. The monitoring apparatus includes a detector 20 which measures a photo-thermal response from the ion-implanted sample which has been irradiated by a laser beam as shown in FIG. 1, and a complex conversion coefficient counter 22 for counting a complex conversion coefficient from the result value measured from the detector 20. In addition, the monitoring apparatus includes a linearizer 24 including a processor 25 for counting the moving distance of the traces of each complex conversion coefficient value on a complex coordinate, and linearizing it for the dose. The monitoring apparatus may also include a display 26 for displaying the changes of the dose of the ion-implantation process based on the linearized moving distance of the traces.

Thus, the detector 20 performs step (S4), the counter 22 performs step (S6), the processor 25 performs steps (S8)–(S12) and the display 26 display the graph from step (S14). Steps (S6)–(S14) may all be performed by a single processor.

Therefore, based on the analysis standard of the above ion-implantation process referring to the graph in FIG. 6, signals are detected from the ion-implantation sample so that the dose of the ion-implantation process or the energy can be precisely analyzed. In other words, once calibration according to a variation of a parameter of interest, e.g. dose or energy, has been performed at set levels, additional measurements of unknown samples can precisely determine the value of the parameter of interest.

Therefore, according to the present invention, process conditions of ion-implantation process can be exactly analyzed by processing signals detected from an ion-implanted sample during a specific ion-implantation process, and comparing with the results acquired as above, i.e. based on the correlation of the main process conditions of the ion-implantation process, such as dose or energy, and the linearized moving distance of the traces of complex conversion coefficient, thereby making it possible to precisely manage the process, and maximizing the production yield.

Still further, while the present invention has been described in detail, it should be understood that various changes, substitutions and alterations can be made thereto without departing from the spirit and scope of the invention as defined by the appended claims.

What is claimed is:

1. A method of monitoring an ion-implantation process using photo-thermal response from an ion-implanted sample, the method comprising:

a) counting a complex conversion coefficient from the each result value measured for the photo-thermal response by irradiating a laser beam on the sample into which ions are implanted by changing a specific process condition of the ion-implantation process;

b) linearizing a specific parameter of complex conversion coefficient for each complex conversion coefficient according to the changes of the specific process condition; and c) monitoring a value of the specific process condition of the ion-implantation process based on a detected value of the specific parameter which is linearized according to the changes of the specific process condition.

2. The method of claim 1, wherein the specific process condition of the ion-implantation process which is changed is a dose of ions.

3. The method of claim 1, wherein the specific process condition of the ion-implantation process which is changed is an energy of ions.

4. The method of claim 1, wherein the specific parameter of the complex conversion coefficient which is linearized is a distance between each indicating point of each of the complex conversion coefficient in complex coordinates.

5. The method of claim 4, wherein said linearizing a specific parameter of each complex conversion coefficient according to the changes of the a process condition comprise:

b1) designating each of the complex conversion coefficients in complex coordinates;

b2) detecting the traces between each of the end points of the complex conversion coefficients in complex coordinates;

b3) counting a moving distance of the traces between each end point responsive to the changes of the specific process condition; and b4) plotting the moving distance of the traces between each end point responsive to the changes of the specific process condition on a graph.

6. The method of claim 5, wherein said detecting the traces between each of the indicating points of the complex conversion coefficients includes converting the end point of each of the complex conversion coefficients designated in complex coordinates into a rectangular coordinate value (X,Y) in rectangular coordinates.

7. The method of claim 5, wherein said counting the moving distance of the traces includes setting an initial value corresponding to an initial condition of the specific process condition, which is changed, and summing the initial value and an increase of the moving distance, the sum serving as the moving distance of the traces according to the changes of the specific process condition.

8. The method of claim 1, wherein the moving distance of the traces, which is shown as a graph, is designated as first order function, which is in one-to-one correspondence with the changes of the specific process condition.

9. A monitoring apparatus of ion-implantation process using photo-thermal response from an ion-implanted sample, wherein the ion-implanted sample is irradiated with a laser beam, the monitoring apparatus comprising:

a detector which measures a photo-thermal response from the ion-implanted sample irradiated by the laser beam;

a complex conversion coefficient counter which counts a complex conversion coefficient from a plurality of result values measured by the detector, the plurality of result values being detected after a corresponding plurality of changes of a specific process condition of the ion-implantation process; and a linearizer which linearizes a specific parameter of complex conversion coefficient for each of the complex conversion coefficients according to the variance of the specific process condition of the ion-implantation process.

10. The monitoring apparatus of claim 9, wherein the specific process condition of the ion-implantation process, which is changed, is a dose of implanted ions.

11. The monitoring apparatus of claim 9, wherein the specific process condition of the ion-implantation process, which is changed, is the energy of implanted ions.

12. The monitoring apparatus of claim 9, wherein the specific parameter of the complex conversion coefficients is a moving distance of the traces of each end point of the complex conversion coefficients.

13. The monitoring apparatus of claim 12, wherein the linearizer comprises a processor which designates each of the complex conversion coefficients on a complex coordinates, determines the traces between adjacent end-points of the complex conversion coefficients in complex coordinates, and counts the moving distance between each end point of the complex conversion coefficient on the traces according to the variance of the specific process condition.

14. The monitoring apparatus of claim 13, wherein said determining the traces of each end point of the complex conversion coefficient by the processor includes converting the indicating point of each of the complex conversion coefficient, which is designated in complex coordinates, into a rectangular coordinate value (X,Y) in rectangular coordinates.

15. The monitoring apparatus of claim 13, wherein said processor further generates a graphical representation of the moving distance of the end points on the traces according to the variance of the specific process condition.

16. The monitoring apparatus of claim 13, wherein said processor further sets an initial value corresponding to an initial specific process condition and adds the initial value to the change in moving distance to obtain the moving distance for a current specific process condition.

17. The monitoring apparatus of claim 9, further comprising a display which displays the changes of a specific process condition of the ion-implantation process based on a specific parameter which is linearized by the linearizer.

* * * * *